(12) United States Patent
Rakshit

(10) Patent No.: US 11,864,908 B2
(45) Date of Patent: Jan. 9, 2024

(54) ANALYZING SENSOR DATA FOR EARLY DETECTION OF MEDICAL CONDITIONS

(71) Applicant: INTERNATIONAL BUSINESS MACHINES CORPORATION, Armonk, NY (US)

(72) Inventor: Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1076 days.

(21) Appl. No.: 16/193,484

(22) Filed: Nov. 16, 2018

(65) Prior Publication Data

US 2020/0155058 A1 May 21, 2020

(51) Int. Cl.
*A61B 5/00* (2006.01)
*G16H 50/20* (2018.01)
*G06Q 10/1093* (2023.01)
*A61B 5/11* (2006.01)

(52) U.S. Cl.
CPC .......... *A61B 5/4362* (2013.01); *A61B 5/0011* (2013.01); *A61B 5/0022* (2013.01); *A61B 5/1104* (2013.01); *A61B 5/7282* (2013.01); *A61B 5/746* (2013.01); *G06Q 10/1095* (2013.01); *G16H 50/20* (2018.01); *A61B 2503/02* (2013.01)

(58) Field of Classification Search
CPC ... A61B 5/0011; A61B 5/0022; A61B 5/1104; A61B 5/4362; A61B 5/7282; A61B 5/746; A61B 2503/02; G16H 40/60; G16H 50/20; G06Q 10/1095
See application file for complete search history.

(56) References Cited

U.S. PATENT DOCUMENTS

| 7,016,722 | B2 | 3/2006 | Prichep | |
|---|---|---|---|---|
| 2004/0162504 | A1 | 9/2004 | Fatemi | |
| 2007/0130287 | A1* | 6/2007 | Kumar | G16H 15/00 |
| | | | | 709/217 |
| 2011/0015471 | A1 | 1/2011 | Galt | |

(Continued)

FOREIGN PATENT DOCUMENTS

EP          2055235         5/2009

OTHER PUBLICATIONS

Shahidullah, Sara et al., "Prenatal hearing tests?", 1993, Journal of Reproductive and Infant Psychology, vol. 11 (3) pp. 143-146 (Year: 1993).*

(Continued)

*Primary Examiner* — Patrick Fernandes
*Assistant Examiner* — Anna Roberts
(74) *Attorney, Agent, or Firm* — Rakesh Roy; Andrew D. Wright; Calderon Safran & Cole, P.C.

(57) ABSTRACT

A computer-implemented method includes: monitoring, by a computing device, exposed stimuli based on sensor data; monitoring, by the computing device, a response to the stimuli based on the sensor data; detecting, by the computing device, a deviation between the response to the stimuli and an expected response to the stimuli, wherein the expected response to the stimuli is determined based on information stored by a knowledge corpus; and executing, by the computing device, a deviation instruction based on the detecting the deviation.

20 Claims, 8 Drawing Sheets

(56) References Cited

U.S. PATENT DOCUMENTS

| | | | | |
|---|---|---|---|---|
| 2016/0174840 | A1* | 6/2016 | Udoh | A61B 5/0059 600/595 |
| 2016/0270670 | A1* | 9/2016 | Oz | A61B 5/282 |
| 2017/0337341 | A1 | 11/2017 | Palanichamy et al. | |
| 2018/0000405 | A1* | 1/2018 | Penders | A61B 5/1118 |
| 2018/0146868 | A1* | 5/2018 | Pon | A61B 8/0866 |

OTHER PUBLICATIONS

Granier-Deferre, C et al. "Feasibility of Prenatal Hearing Test", 1985, Acta Otolaryngol, vol. 99 (421) pp. 93-101 (Year: 1985).*

Lever, "Laclan's first hearing aids 7 weeks old. Our gorgeous baby boy", https://www.youtube.com/watch?v=UUP02yTKWWo, YouTube, Aug. 31, 2014, 1 page.

Anonymous, "Protect your unborn baby against hearing loss", https://www.hear-it.org/Protect-your-unborn-baby-against-hearing loss, hear-it, accessed Oct. 12, 2018, 2 pages.

Kochrekar, "Hearing Problems In Pregnancy—Causes, Symptoms & Treatments", http://www.momjunction.com/articles/hearing-problems-in-pregnancy_00374430/#gref, momjunction.com, Dec. 1, 2015, 4 pages.

Macrae, "Mother's blood test could be used to predict disorders in unborn baby", http://www.dailymail.co.uk/health/article-1337025/Mothers-blood-test-used-predict-disorders-unborn-baby.html, DailyMail UK, Dec. 8, 2010, 3 pages.

Anonymous, "Understand Prenatal, Perinatal and Postnatal Causes of Hearing Loss—Sound Steps", http://soundsteps.in/causes of-hearing-loss, SoundStep, accessed Oct. 12, 2018, 3 pages.

Anonymous, "NIH Fact Sheets—Newborn Hearing Screening", https://report.nih.gov/NIHfactsheets/ViewFactSheet. aspx?csid=104, NIH.gov, accessed Oct. 12, 2018, 2 pages.

Arora, "6 amazing facts about your baby's kicks", http://www.thehealthsite.com/pregnancy/your-babys-kicks-6-amazing-facts-d214/, TheHealthSite.com, Feb. 2, 2015, 2 pages.

Arora,"All you need to know about your baby's kicks during pregnancy", http://www.thehealthsite.com/pregnancy/all-you-need-to-know-about-your-babys-kicks-during-pregnancy/, TheHealthSite.com, Oct. 10, 2014, 3 pages.

Howland, "When Can You Feel the Baby Move? Unpacking Quickening in Pregnancy", https://www.mamanatural.com/when-can-you-feel-the-baby-move/, Mamanatural.com, Jan. 29, 2018, 6 pages.

McCulloch, "Baby Kicking—9 Facts You Need To Know", https://www.bellybelly.com.au/pregnancy/baby-kicking-9-facts-you-need-to-know/, Bellybelly.com, Sep. 18, 2015, 5 pages.

Marsal, "Ultrasonic assessment of fetal activity", https://www.ncbi.nlm.nih.gov/pubmed/6360464, Dec. 1983, 2 pages.

Megan, "15 Hilarious Ways Mother's Describe the Feeling of a Baby Kicking", https://www.babygaga.com/15-hilarious-ways-mothers-describe-the-feeling-of-a-baby-kicking/, BabyGaga.com, Feb. 1, 2017, 4 pages.

Anonymous, "Fetal Movement: Feeling Baby Kick", https://www.medicinenet.com/fetal_movement_feeling_baby_kick_week-by-week/article.htm, Medicinenet.com, accessed Nov. 15, 2018, 4 pages.

BabyCenter Staff, "Music and your unborn child", https://www.babycenter.com/0_music-and-your-unborn-child_6547.pc, babycenter.com, Apr. 17, 2015, 3 pages.

Anonymous, "Can my baby hear if I read and play music to my bump?", https://www.babycentre.co.uk/x1049485/can-my-baby-hear-if-i-read-and-play-music-to-my-bump, babycentre.co.uk, accessed Oct. 12, 2018, 5 pages.

Saenz, "The 10 Most Amazing Electronic Clothes Of the Century", https://singularityhub.com/2010/04/06/the-10-most-amazing-electronic-clothes-of-the-century/, singularityhub.com, Apr. 6, 2010, 7 pages.

Anonymous, "E-textiles", https://en.wikipedia.org/wiki/E-textiles, Wikipedia, accessed Oct. 12, 2018, 8 pages.

National Science Foundation, "Electronic Tattoo—Science of Innovation", https://www.youtube.com/watch?v=4oeFBGFzcrg, YouTube, Dec. 13, 2013, 1 page.

Mell et al., "The NIST Definition of Cloud Computing", NIST, Special Publication 800-145, Sep. 2011, 7 pages.

\* cited by examiner

ANALYZING SENSOR DATA FOR EARLY DETECTION OF MEDICAL CONDITIONS

BACKGROUND

The present invention generally relates to analyzing sensor data for early detection of medical conditions, and more particularly to analyzing sensor data for early detection of medical conditions in an unborn child.

Sensors are used to gather various data, such as sound levels, light levels, vibration patterns, biometrics data, etc. Sensors are implemented in various types of computing devices to gather data associated with individuals. For example, sensors can be implemented in user devices, Internet of Things (IoT) devices, smart phones, electronic tattoos, and wearable computing devices, such as smart rings, smart watches, smart clothing, smart eye glasses, smart contact lenses, etc.

SUMMARY

In an aspect of the invention, a computer-implemented method includes: monitoring, by a computing device, stimuli exposed to an unborn child based on sensor data; monitoring, by the computing device, a response by the unborn child to the stimuli based on the sensor data; detecting, by the computing device, a deviation between the response to the stimuli and an expected response of the unborn child to the stimuli, wherein the expected response to the stimuli is determined based on information stored by a knowledge corpus; and executing, by the computing device, a deviation instruction based on the detecting the deviation.

In an aspect of the invention, there is a computer program product including a computer readable storage medium having program instructions embodied therewith. The program instructions are executable by a computing device to cause the computing device to: receive and monitor sensor data corresponding to movement patterns of an unborn child; determine stimuli associated with the movement patterns based on the sensor data; generate a plurality of records, each having a dataset identifying the stimuli, corresponding movement patterns associated with the stimuli, and health condition information; provide the plurality of records for storage in a knowledge corpus; identify a health condition in a different unborn child based on actual responses to the stimuli and expected responses to the stimuli stored by the knowledge corpus; and execute an action based on the identified health condition.

In an aspect of the invention, a system includes: a processor, a computer readable memory and a computer readable storage medium associated with a computing device; program instructions to determine, based on sensor data gathered by one or more sensor devices, actual responses to stimuli by an unborn child under a set of environmental conditions; program instructions to identify a health condition in the unborn child based on a deviation between the actual responses to stimuli in relation to expected responses to the stimuli under the set of environmental conditions, wherein the expected responses to the stimuli are stored in a knowledge corpus; program instructions to execute a computer-executable instruction based on the identifying the health condition. The program instructions are stored on the computer readable storage medium for execution by the processor via the computer readable memory.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

Figure 1:
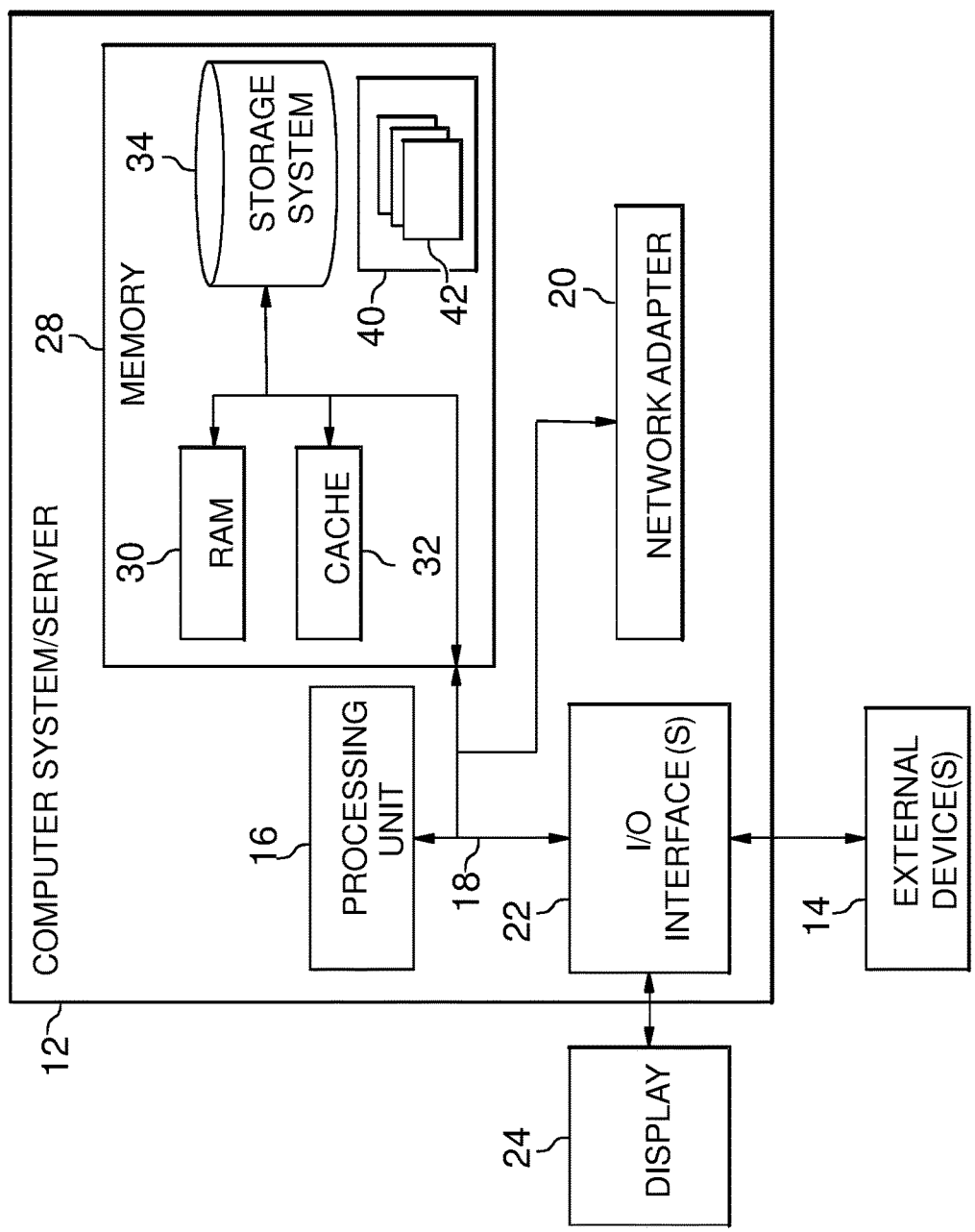
FIG. 1 depicts a cloud computing node according to an embodiment of the present invention.

The present invention generally relates to analyzing sensor data for early detection of medical conditions, and more particularly to analyzing sensor data for early detection of medical conditions in an unborn child. Early detection of medical conditions in an unborn child is useful in helping medical professionals and parents in proactively treating and/or preparing for the unborn child. Advantageously, aspects of the present invention provide a method and/or system by which a medical condition (e.g., a hearing-impairment condition, vision-impairment, condition, gestational diabetes, and/or other medical condition) is detected in an unborn child.

As described herein and in accordance with aspects of the present invention, a knowledge corpus is created over a period of time in which the knowledge corpus stores sensor data, in a structured format, that identifies expected responses to stimuli and environmental conditions that are associated with a healthy child. In embodiments, the knowledge corpus is generated by gathering sensor data of participants (e.g., pregnant women) wearing various types of wearable sensor devices (e.g., smart watches/ring/eyewear, electronic tattoos, smart clothing, etc.) to gather movement/kick pattern data associated with unborn children. The health condition of a child, after birth, is then associated with associated sensor data that has been gathered throughout the pregnancy term. In this way, the knowledge corpus stores data sets that are associated with the health condition of a child.

As an illustrative example, in embodiments, the knowledge corpus stores a dataset of sensor data indicating the child's movement patterns when the child is exposed to particular stimuli (e.g., a certain level of light and sound) under a certain set of environmental conditions (e.g., at a certain time of day, under certain temperature/weather conditions, etc.). Further, the knowledge corpus stores information indicating that the child's condition associated with the dataset (e.g., whether the dataset is associated with a health child or a child with a medical condition).

In embodiments, aspects of the present invention use the knowledge corpus to detect a possible medical condition in an unborn child (e.g., after the knowledge corpus has been initially generated). For example, aspects of the present invention continuously monitor a various set of sensor data from which the child's movement patterns (e.g., kicking patterns and/or other movement patterns) is determined. Aspects of the present invention identify the child's response to external stimuli and environmental conditions (e.g., the child's movement patterns after being exposed to an external stimuli), and determine that the child's response deviates from that of a healthy child (e.g., based on the data from the knowledge corpus). As an illustrative example, aspects of the present invention determine that an unborn child may have a hearing loss issue or vision issue if the unborn child is not responding to external stimuli as expected (e.g., if the child is not responding to loud noises and/or bright lights as is expected based on the knowledge corpus).

Based on detecting the medical condition, aspects of the present invention determine one or more treatment-related actions to take depending on the severity and type of medical condition. For example, aspects of the present invention adjust a computer-based medical device to treat the medical condition and/or mitigate the effects of the medical condition. As an illustrative example, aspects of the present invention modify dosage settings in a medication dispensary device (e.g., an insulin pump, a pill dispenser, etc.) based on the detected medical condition. Additionally, or alternatively, aspects of the present invention generate an alert to inform parents and/or medical professionals regarding the medical condition. Additionally, or alternatively, aspects of the present invention interfaces with a computing system to automatically schedule an appointment. Additionally, or alternatively, aspects of the present invention adjust settings on pre-natal care medical devices (e.g., non-stress test devices and/or other types of medical devices) based on detecting the medical condition, the type of medical condition, and/or the severity of the medical condition. In this way, aspects of the present invention are used to proactively treat the medical condition and/or better prepare medical personnel for treatment/delivery of the unborn child, thereby improving the health and delivery of the unborn child. For example, based on detecting a medical condition, birthing plans and/or birthing facilities can be adjusted accordingly.

Aspects of the present invention provide a particular solution to a problem of diagnosing and/or treating medical conditions in an unborn child. Aspects of the present invention leverage the use of rules/criteria to effectuate a solution for diagnosing and/or treating medical conditions in an unborn child. For example, aspects of the present invention implement criteria that, when met, adjust the operations of computer-based medical devices, send alerts, interface with scheduling systems to schedule appointments, etc. Aspects of the present invention gather and monitor potentially millions of different data points to provide the particular solution of diagnosing and/or treating medical conditions in an unborn child in a manner that is not humanly possible through the use of human-based data collection using pen and paper.

While described in terms of detecting a possible medical condition in an unborn child, aspects of the present invention are not so limited. For example, in embodiments, aspects of the present invention are applied to mammals other than humans, e.g., in a veterinary medicine implementation.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
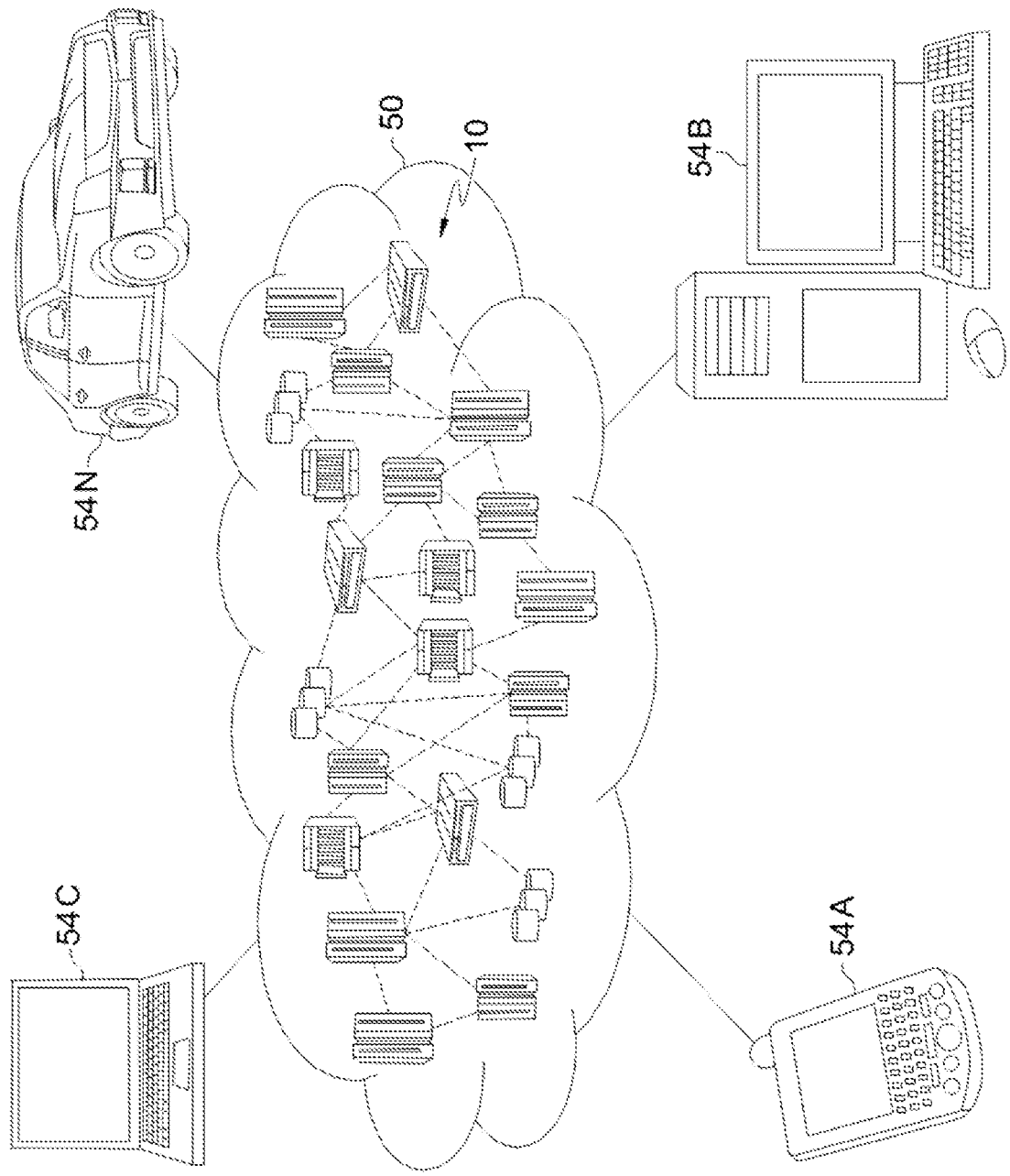
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
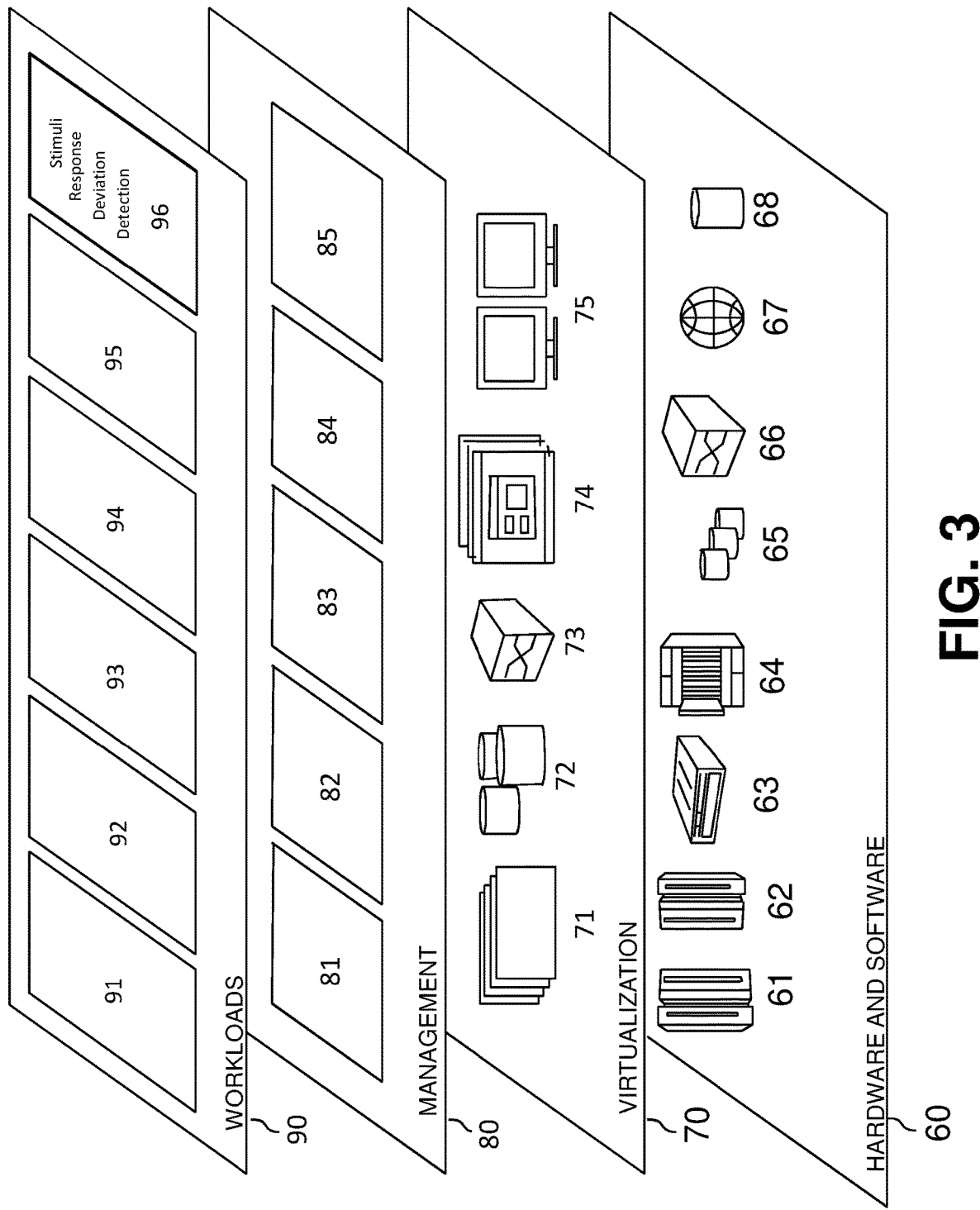
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and stimuli response deviation detection 96.

Referring back to FIG. 1, the program/utility 40 may include one or more program modules 42 that generally carry out the functions and/or methodologies of embodiments of the invention as described herein (e.g., such as the functionality provided by stimuli response deviation detection 96). Specifically, the program modules 42 may monitor movement and responses of an unborn child from health-related data, monitor environmental and stimuli data, detect a deviation in stimuli response, determine a deviation instruction from a set of criteria, and execute the deviation instruction. Other functionalities of the program modules 42 are described further herein such that the program modules 42 are not limited to the functions described above. Moreover, it is noted that some of the modules 42 can be implemented within the infrastructure shown in FIGS. 1-3. For example, the modules 42 may be representative of a health tracking server as shown in FIG. 4.

Figure 4:
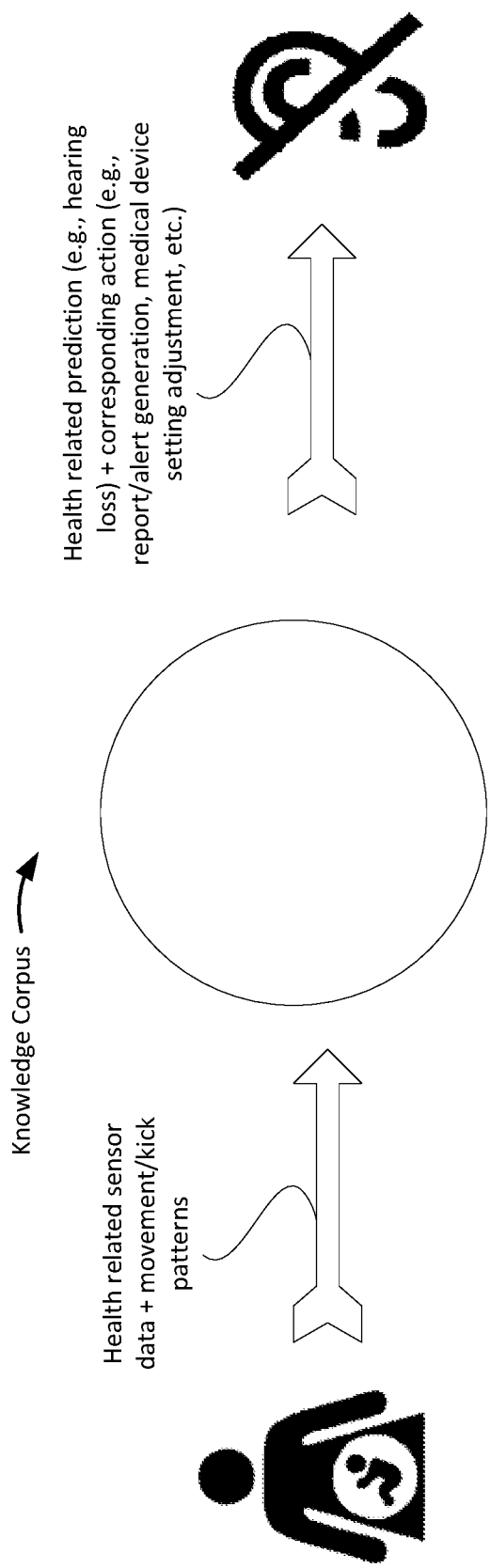
FIG. 4 shows an overview of an example implementation in accordance with aspects of the present invention.

FIG. 4 shows an overview of an example implementation in accordance with aspects of the present invention. As shown in FIG. 4, movement/kick patterns of an unborn child are determined from sensor data (e.g., from sensor devices, such as those implemented in wearable computing devices worn by a mother of the unborn child). The sensor data, combined with data from a knowledge corpus, is used to make a health-related prediction regarding the unborn child (e.g., a prediction of possible hearing loss in the unborn child). For example, the health-related prediction is made by comparing the movement/kick patterns when the unborn child is exposed to a particular environment and stimuli with data in the knowledge corpus storing datasets and corresponding health conditions with those datasets. As an illustrative example, aspects of the present invention determine that an unborn child may have a hearing loss issue if the unborn child is not responding to external stimuli as expected (e.g., if the child is not responding to loud noises as is expected based on the knowledge corpus). As described herein, a corresponding action is determined based on the health-related prediction (e.g., generating an alert, scheduling an appointment with a medical professional, adjusting settings on a medical device, etc.).

As described herein, the knowledge corpus is generated over a period of time by gathering sensor data of participants (e.g., pregnant women) wearing various types of wearable sensor devices (e.g., smart watches/ring/eyewear, electronic tattoos, smart clothing, etc.) to gather movement/kick pattern data associated with unborn children with respect to various influencing factors (e.g., various environments and stimuli). In embodiments, the participants use wearable devices (e.g., smartwatches, smart wristbands, smart ring devices, smart eyewear, etc.) to gather sensor data associated with movement/kick patterns. Additionally, or alternatively, embeddable devices (e.g., an electronic tattoos) are used. For example, an appropriate placed electronic tattoo tracks the increase in the surface of and movement pattern/position of the participant's stomach, which signifies the movement patterns of the unborn child. In embodiments, the participants use wearable devices to track sensor data, such as smart clothing made of electronic cloths, such that, when the cloth touches the participant's body, the smart clothing tracks the movement of movement of unborn child based on changes in the unborn child.

In embodiments, participants the environment and/or stimuli being exposed to the unborn child is tracked along with movement/kick patterns such that the movement/kick patterns associated with those stimuli are saved in the knowledge corpus to later diagnose a potential health issue in an unborn child. For example, mobile devices can track the sound in the surrounding from an inbuilt microphone. Additionally, or alternatively, an external microphone is also be used. In embodiments, illumination sensors installed in the mobile device and/or wearable device can detect the lighting condition and intensity of light in the surrounding. In embodiments, crowd-sourced data, data from wearable devices, and/or external sensor data (e.g., from surrounding cameras) are used for identifying activity/stimuli exposed to the unborn child.

In embodiments, weather data, time of day, time of year, and/or other environmental data is tracked along with movement/kick pattern. While creating knowledge corpus of movement and kick patterns, the sensor data from various devices will be gathered to include movement patterns of the participant's stomach (indicative of the movement patterns of the unborn child), along with stimuli and environmental conditions, such as sound, light and associated loudness, etc. In embodiments, time stamps of each and every sensor feed will be gathered. In addition to data from the sensor feed, research papers on the movement pattern of unborn children in the womb and ultrasound scan images of unborn children will also be considered and factored into the knowledge corpus for diagnosing potential health conditions.

While creating the knowledge corpus, additional testing reports can also be considered (e.g., blood test reports, etc.). In embodiments, any suitable data cleansing/pruning technique is used before using the gathered data for storage in the knowledge corpus. For example, in embodiments, data is ignored if a stomach movement is not related to movement or kick of the unborn child. When there is a movement or kick of the unborn child, the participant will feel a biometric sensation, and the knowledge corpus stores the rate of change in biometric parameters (e.g., blood flow, heart rate, etc.), which can be used for identifying which movement of the stomach is related to movement or kick and not another type of stomach movement.

Using cognitive computing techniques, an intelligent system creates correlations among various influencing factors with the movement and kick pattern of the unborn child, position and direction of kick and movement etc. Once the knowledge corpus is created, then this information is used for tracking the movement pattern of unborn baby with various external influencing factors (e.g., environment/stimuli). Deviations are detected in the movement/kick patterns with same or similar external influences (e.g., similar environment and stimuli). The degree of deviation is considered to understand how the unborn child is reacting to a stimuli. Any deviation on movement and kick pattern with respect to different types of external influencing factors and stimuli may be considered as point of concern and will be proactively be notifying the doctor for corrective action. For example, aspects of the present invention take any number of corrective actions based on a set of criteria (e.g., deviation criteria). Based on the type of deviation, the degree of the deviation, health of the mother, etc., aspects of the present invention take different corrective actions or execute different deviation instructions.

As described herein, correction actives include providing a report identifying a possible medical condition associated with the deviation, adjusting medical equipment operations, scheduling appointments with medical providers, etc. In this way, aspects of the present invention are used to proactively treat the medical condition and/or better prepare medical personnel for treatment/delivery of the unborn child, thereby improving the health and delivery of the unborn child. For example, based on detecting a medical condition, birthing plans and/or birthing facilities can be adjusted accordingly.

Figure 5:
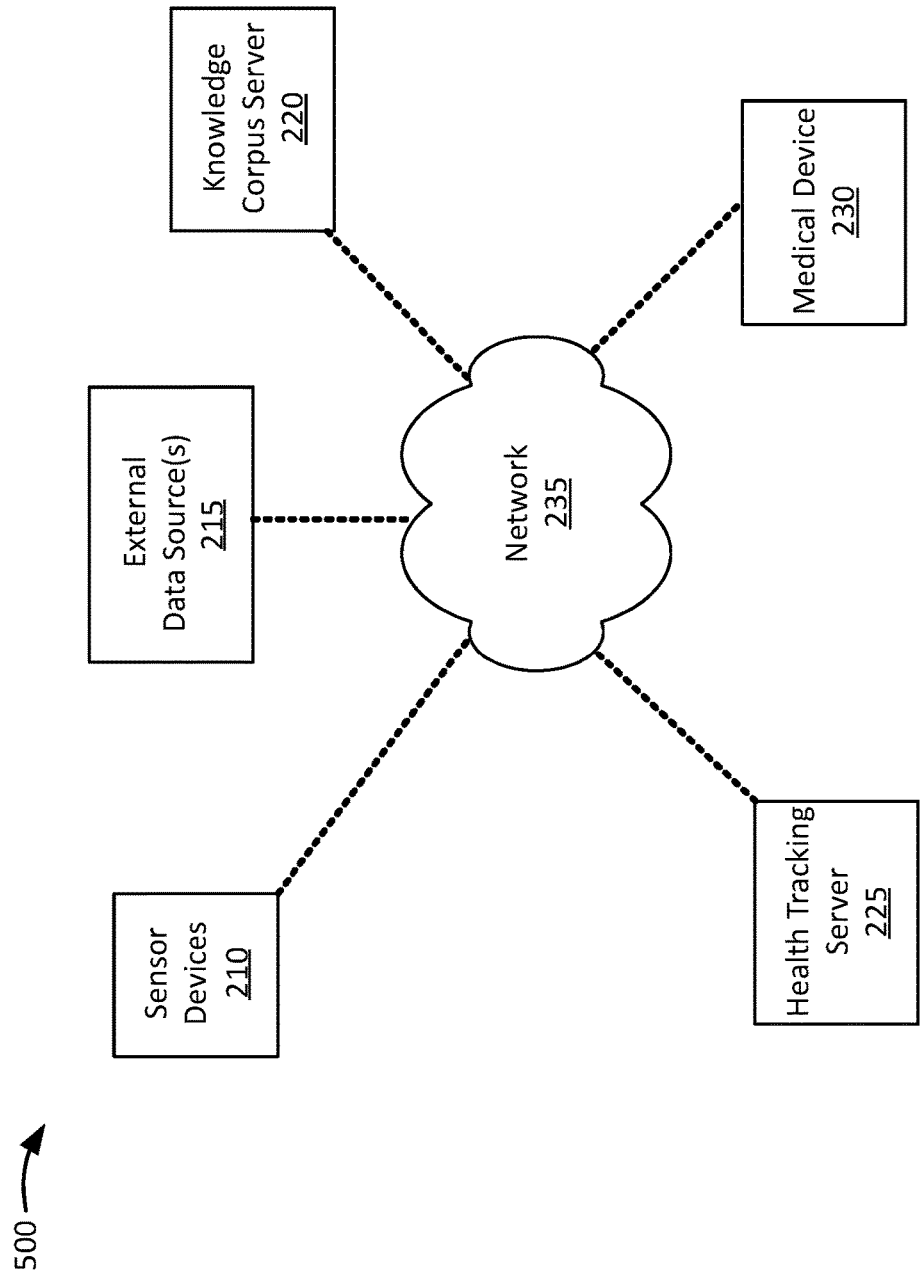
FIG. 5 shows an example environment in accordance with aspects of the present invention.

FIG. 5 shows an example environment in accordance with aspects of the present invention. As shown in FIG. 5, environment 500 includes sensor devices 210, one or more external data sources 215, a knowledge corpus server 220, a health tracking server 225, a medical device 230, and a network 235. In embodiments, one or more components in environment 500 may correspond to one or more components in the cloud computing environment of FIG. 2. In embodiments, one or more components in environment 500 may include the components of computer system/server 12 of FIG. 1.

The sensor devices 210 include one or more sensors (e.g., movement sensors, object sensors, biometric sensors, accelerometers, etc.), cameras, audio input devices, Internet of Things (IoT) devices, etc. that collect data corresponding to movement/kick patterns of an unborn child. Additionally, or alternatively, the sensor devices 210 gather data regarding the environment and/or stimuli exposed to the unborn child. In embodiments, the sensor devices 210 are implemented within user devices (e.g., smart phones) associated with a participant (e.g., pregnant woman) or wearable computing devices worn by the participant (smart watches/ring/eyewear, electronic tattoos, smart clothing, etc.). Additionally, or alternatively, the sensor devices 210 are implemented externally to the participant. For example, in embodiments, the sensor devices 210 include external cameras and/or crowd-sourced data devices which are used to obtain environmental data surrounding the participant.

The external data source 215 includes one or more computing devices (e.g., such as computer system/server 12 of FIG. 1) that collects, stores, and provides non-sensor related data that, along with sensor data gathered by the sensor devices 210, can be used to diagnose health conditions of an unborn child. For example, in embodiments, the external data source 215 collects, stores, and provides research papers on the movement pattern of unborn children in the womb. Additionally, or alternatively, the external data source 215 collects, stores, and provides ultrasound scan images of an unborn children. Additionally, or alternatively, the external data source 215 collects, stores, and provides other non-sensor related data associated with the diagnosis of a possible health condition for an unborn child.

The knowledge corpus server 220 includes one or more computing devices (e.g., such as computer system/server 12 of FIG. 1) that stores a knowledge corpus having datasets of sensor data relating to movement and kick patterns of an unborn child, environment and stimuli associated with the movement and kick patterns. Further, the knowledge corpus server 220 stores corresponding health conditions associated with those datasets. Additionally, or alternatively, the knowledge corpus, stored and maintained by the knowledge corpus server 220, includes external source data obtained from the external data source 215. As described herein, the knowledge corpus stores a data structure including data relating to the movement/kick responses of an unborn child when the unborn child is exposed to certain stimuli in a particular environment. The data structure of the knowledge corpus stores information identifying whether the movement and kick responses are considered "normal" (e.g., no health issues). In embodiments, the knowledge corpus stores information used to diagnose a health condition based on the movement and kick responses to stimuli in certain conditions.

The health tracking server 225 includes one or more computing devices (e.g., such as computer system/server 12 of FIG. 1) that monitors movement and responses of an unborn child from sensor data (e.g., gathered by the sensor devices 210), monitors environmental and stimuli data (e.g., gathered by the sensor devices 210), and detects a deviation in stimuli response (e.g., a deviation in the stimuli response stored by the knowledge corpus). As described herein, a deviation in the stimuli response from the stimuli response stored by the knowledge corpus may indicate a possible health issue in the unborn child. As an example, the deviation may be indicative of a hearing loss issue, a vision issue, and/or other type of medical related issue. In embodiments, the health tracking server 225 determines a deviation instruction from a set of criteria, and executes the deviation instruction (e.g., to take a corresponding action based on determining the deviation and possible health issue).

The medical device 230 includes one or more medical-based computing devices (e.g., such as computer system/server 12 of FIG. 1) that performs medical operations. In embodiments, the medical device 230 includes a medication dispenser (e.g., pill dispenser, insulin/medicine pump etc.). In embodiments, the medical device 230 receives an instruction to adjust its operations from the health tracking server 225 (e.g., when the health tracking server 225 detects a deviation in stimuli response indicating a possible health issue with an unborn child). In embodiments, the medical device 230 includes a medical scheduling system which receives scheduling instructions from the health tracking server 225 (e.g. to schedule an appointment with a health-care professional in response to the health tracking server 225 detecting a possible health issue with an unborn child).

The network 235 may include network nodes, such as network nodes 10 of FIG. 2. Additionally, or alternatively, the network 235 may include one or more wired and/or wireless networks. For example, the network 235 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network 235 may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks.

The quantity of devices and/or networks in the environment 500 is not limited to what is shown in FIG. 5. In practice, the environment 500 may include additional devices and/or networks; fewer devices and/or networks; different devices and/or networks; or differently arranged devices and/or networks than illustrated in FIG. 5. Also, in some implementations, one or more of the devices of the environment 500 may perform one or more functions described as being performed by another one or more of the devices of the environment 500. Devices of the environment 500 may interconnect via wired connections, wireless connections, or a combination of wired and wireless connections.

Figure 6:
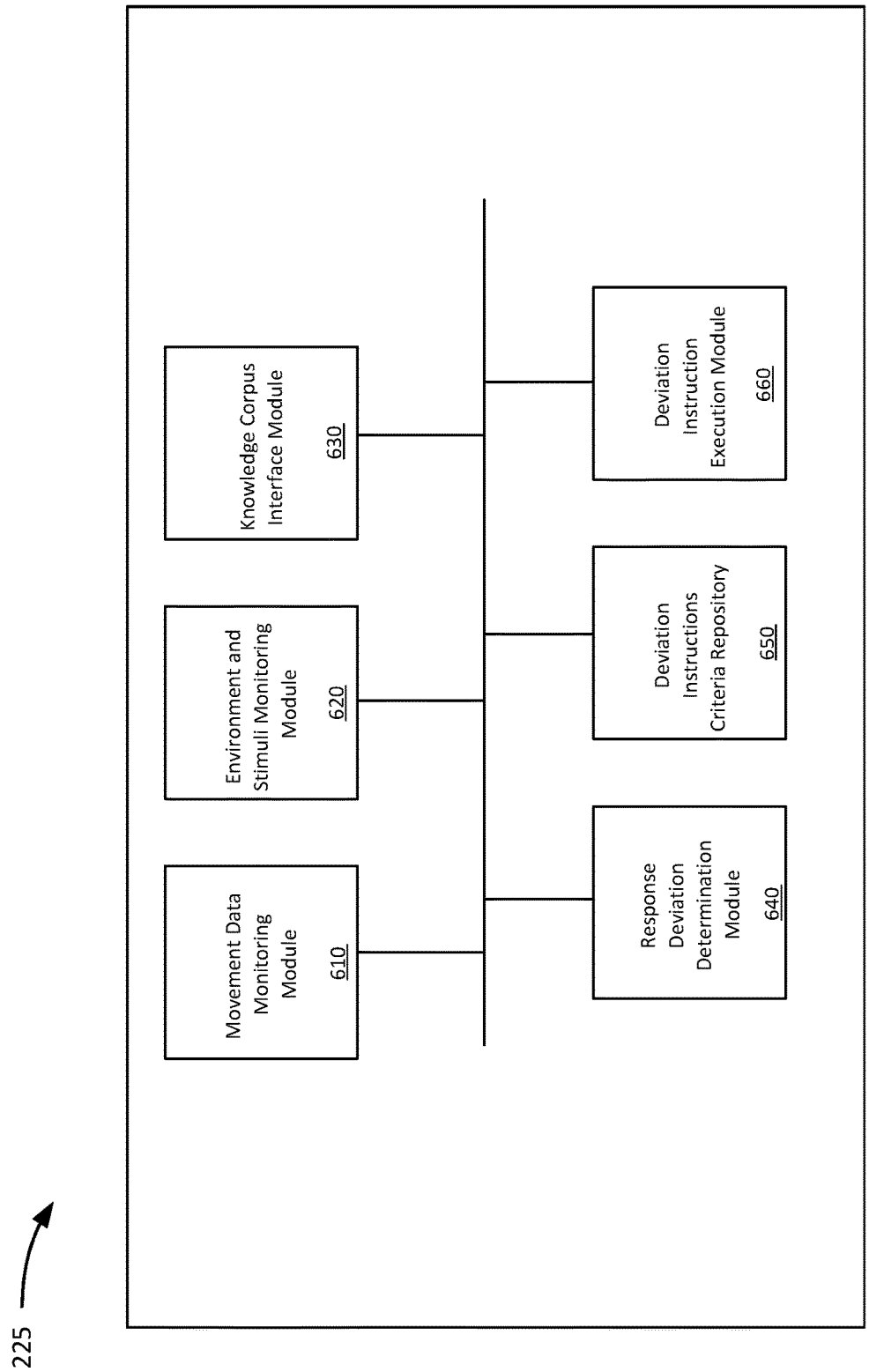
FIG. 6 shows a block diagram of example components of a health tracking server in accordance with aspects of the present invention.

FIG. 6 shows a block diagram of example components of a health tracking server in accordance with aspects of the present invention. As shown in FIG. 6, the health tracking server 225 includes a movement data monitoring module 610, an environment and stimuli monitoring module 620, a knowledge corpus interface module 630, a response deviation determination module 640, a deviation instructions criteria repository 650, and a deviation instruction execution module 660. In embodiments, the health tracking server 225 may include additional or fewer components than those shown in FIG. 6. In embodiments, separate components may be integrated into a single computing component or module. Additionally, or alternatively, a single component may be implemented as multiple computing components or modules.

The movement data monitoring module 610 includes a program module (e.g., program module 42 of FIG. 1) that receives and monitors movement data gathered by the sensor devices 210. For example, the movement data monitoring module 610 obtains sensor data from the sensor devices 210 for determining movement/kick patterns of an unborn child as part of building/updating a knowledge corpus and/or detecting a possible health issue in an unborn child.

The environment and stimuli monitoring module 620 includes a program module (e.g., program module 42 of FIG. 1) that receives and monitors environment and stimuli data gathered by the sensor devices 210. For example, the environment and stimuli monitoring module 620 obtains sensor data from the sensor devices 210 for and determines the environment and stimuli associated with the sensor data. In embodiments, the environment and stimuli monitoring module 620 generates time-stamped records that associate the movement data with the environment and stimuli data.

The knowledge corpus interface module 630 includes a program module (e.g., program module 42 of FIG. 1) that interfaces with the knowledge corpus server 220 to store, access, and/or update information in the knowledge corpus. For example, in embodiments, the knowledge corpus interface module 630 provides, to the knowledge corpus server 220, records that associate movement data with environment and stimuli data, as well as associated health conditions (e.g., as part of building/updating the knowledge corpus). In embodiments, the knowledge corpus interface module 630 accesses the knowledge corpus data structure to identify datasets of movement responses to stimuli under certain environmental conditions that are considered normal.

The response deviation determination module 640 includes a program module (e.g., program module 42 of FIG. 1) that determines deviations between responses to stimuli under certain environmental conditions (e.g., based on data obtained by the movement data monitoring module 610 and the environment and stimuli monitoring module 620) and datasets stored by the knowledge corpus. More specifically, the response deviation determination module 640 determines that an unborn child's movement and kick response to a stimuli under certain environmental conditions deviates from the response under similar environmental conditions as stored by the knowledge corpus (thus indicating a potential health condition, such as hearing loss or vision loss in the unborn child).

The deviation instructions criteria repository 650 includes a data storage device (e.g., storage system 34 of FIG. 1) that stores a set of criteria for actions to take based on the deviation detected by the response deviation determination module 640. For example, the deviation instructions criteria repository 650 stores criteria that identifies different actions to take based on the degree of deviation. Additionally, or alternatively, the deviation instructions criteria repository 650 stores criteria based on the type of deviation (e.g., a deviation in kick patters versus a deviation in the unborn child's body/rolling movement patterns, etc.). Additionally, or alternatively, the deviation instructions criteria repository 650 stores criteria for actions to take based on other factors (e.g., external data associated with the deviation) provided by the external data source 215 (e.g., data from research papers, sonogram images, mother's health data, such as biometrics data, blood test reports, etc.). As described herein, example deviation instructions/actions to take include modifying dosage settings and/or other operations of the medical device 230, interfacing with a computer-based scheduling system hosted by the medical device 230 to schedule an appointment with a medical professional, sending alerts to user devices associated with parents and/or medical professionals of the unborn child, etc.

The deviation instruction execution module 660 includes a program module (e.g., program module 42 of FIG. 1) that executes the deviation instructions determined by the deviation instructions criteria repository 650. In this way, the deviation instruction execution module 660 executes a corresponding action when a possible medical condition of an unborn child is detected (e.g., by the response deviation determination module 640).

Figure 7:
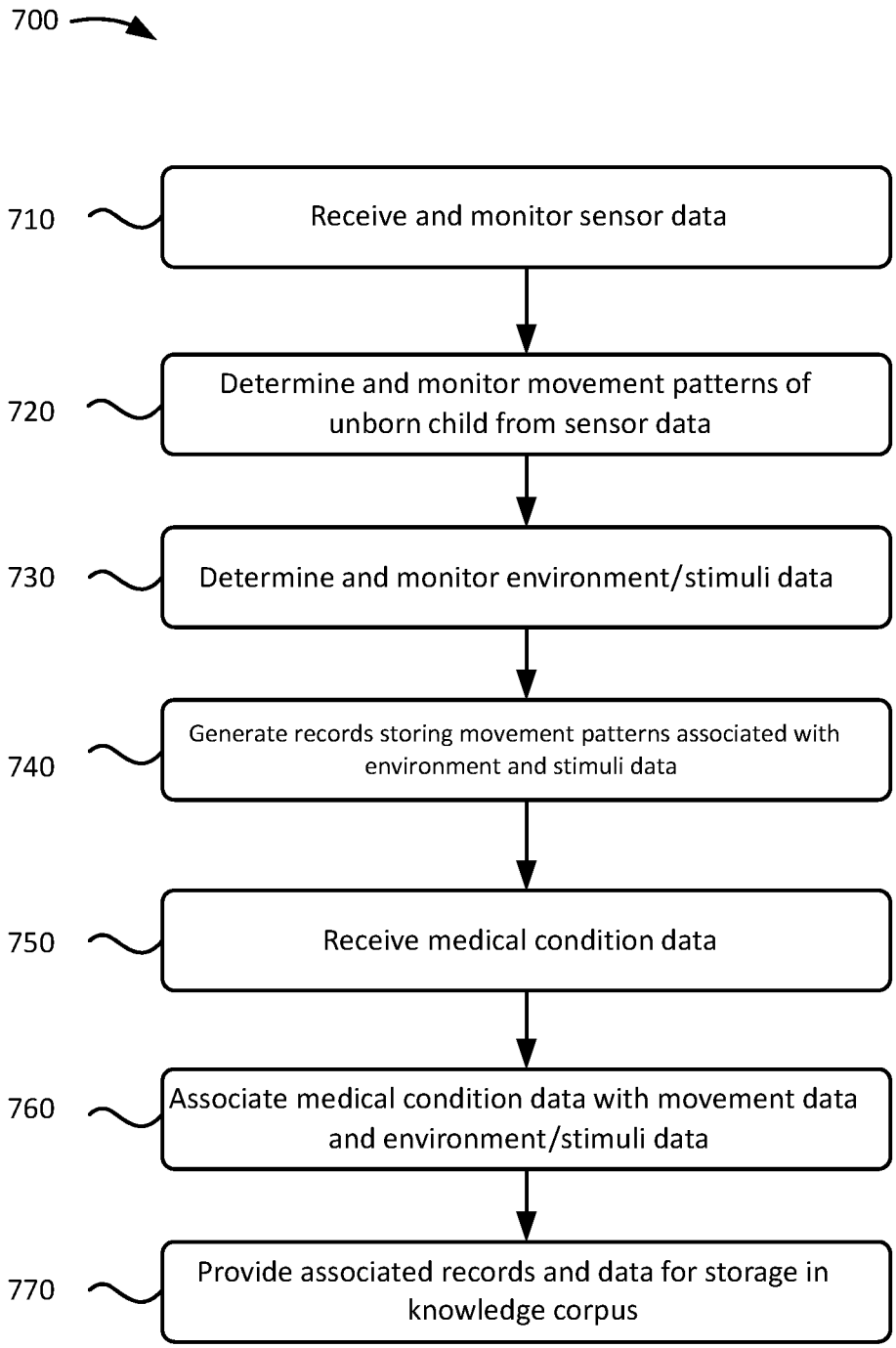
FIG. 7 shows an example flowchart of a process for building and/or updating a knowledge corpus to be used for detecting possible health conditions in an unborn child in accordance with aspects of the present invention.

FIG. 7 shows an example flowchart of a process for building and/or updating a knowledge corpus to be used for detecting possible health conditions in an unborn child. The steps of FIG. 7 may be implemented in the environment of FIG. 5, for example, and are described using reference numbers of elements depicted in FIG. 5. As noted above, the flowchart illustrates the architecture, functionality, and operation of possible implementations of systems, methods, and computer program products according to various embodiments of the present invention.

As shown in FIG. 7, process 700 includes receiving and monitoring sensor data (step 710). For example, as described above with respect to the movement data monitoring module 610 and the environment and stimuli monitoring module 620, the health tracking server 225 receives and monitors sensor data gathered by the sensor devices 210. As described herein, the sensor data is gathered from participants (e.g., pregnant women) wearing various types of wearable sensor devices 210 (e.g., smart watches/ring/eyewear, electronic tattoos, smart clothing, etc.).

Process 700 also includes determining and monitoring movement patterns of the unborn child from the sensor data (step 720). For example, as described above with respect to the movement data monitoring module 610, the health tracking server 225 determines movement/kick patterns of an unborn child based on monitoring the sensor data. For example, sensor devices 210 in the form of electronic tattoos, wearable devices, etc. tracks the increase in the surface of and movement pattern/position of the participant's stomach, which signifies the movement patterns of the unborn child.

Process 700 further includes determining and monitoring environment/stimuli data (step 730). For example, as described above with respect to the environment and stimuli monitoring module 620, the health tracking server 225 determines the environment and stimuli associated with the sensor data, such as lighting conditions/stimuli, noise conditions/stimuli, vibration stimuli, weather conditions, time of day/year, etc.

Process 700 also includes generating records storing movement patterns associated with environment and stimuli data (step 740). For example, as described above with respect to the environment and stimuli monitoring module 620, the health tracking server 225 generates time-stamped records that associate the movement data with the environment and stimuli data. In this way, the records identify the unborn child's responses to external stimuli under particular environmental conditions.

In embodiments, steps 710-740 are repeated for each participant over a period of time so that a multitude of data records are stored documenting the movement/kick patterns and responses to stimuli under different environmental conditions.

Process 700 further includes receiving medical condition data (step 750). For example, for a particular participant, the health tracking server 225 receives medical condition data indicating the medical condition of the child postpartum. Using the medical condition data, the records (e.g., from step 740) are updated to indicate whether the data from these records indicate responses/movements of an unborn child with a health condition (and which health condition) or without a health condition.

Process 700 also includes associating the medical condition data with the movement data and environment/stimuli data (step 760). For example, the health tracking server 225 updates the records (e.g., from step 740) to associate the medical condition data of the child with the data indicating the responses to stimuli under different environmental conditions. In this way, the dataset stored by the records (e.g., from step 740) is associated with a corresponding medical condition.

Process 700 further includes providing the associated records and data for storage in the knowledge corpus (step 770). For example, as described above with respect to the response deviation determination module 640, the health tracking server 225 provides the records and associated data (e.g., from steps 740-760) to the knowledge corpus server 220 for storage in the knowledge corpus. In this way, the dataset from the records (e.g., from steps 740-760) is included in the knowledge corpus for diagnosing future medical problems in other unborn children. As described herein, process 700 is repeated for each participant to continue to build and update the knowledge corpus.

Figure 8:
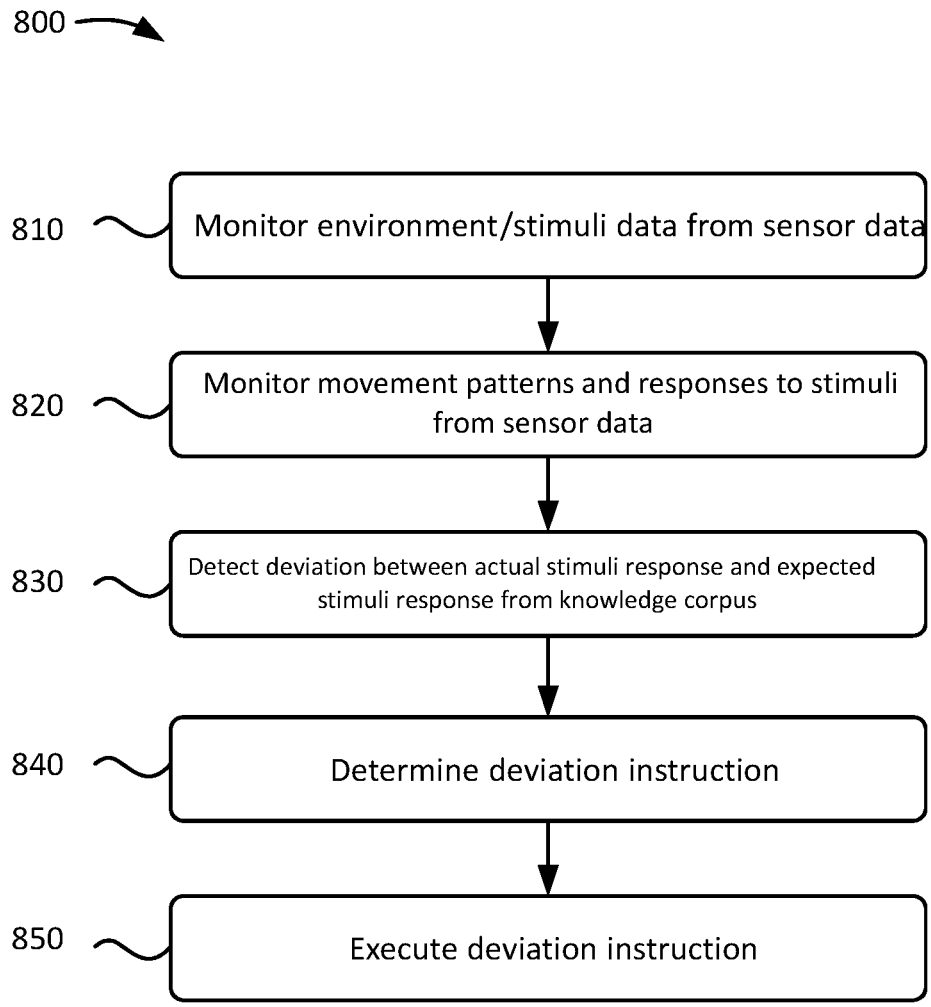
FIG. 8 shows an example process for identifying a possible health condition health condition in an unborn child based on sensor data and performing a corresponding action based on identifying the possible health condition in accordance with aspects of the present invention.

FIG. 8 shows an example process for identifying a possible health condition health condition in an unborn child based on sensor data and performing a corresponding action based on identifying the possible health condition in accordance with aspects of the present invention. The steps of FIG. 8 may be implemented in the environment of FIG. 5, for example, and are described using reference numbers of elements depicted in FIG. 5. As noted above, the flowchart illustrates the architecture, functionality, and operation of possible implementations of systems, methods, and computer program products according to various embodiments of the present invention.

As shown in FIG. 8, process 800 includes monitor environment/stimuli data from sensor data (step 810). For example, as described above with respect to the environment and stimuli monitoring module 620, the health tracking server 225 monitors environment and stimuli data from the sensor data gathered by the sensor devices 210. More specifically, the health tracking server 225 identifies stimuli exposed to an unborn child and the environmental conditions of under which those stimuli are exposed.

Process 800 also includes monitoring movement patterns and responses to the stimuli from the sensor data (step 820). For example, as described above with respect to the movement data monitoring module 610, the health tracking server 225 monitors movement/kick patterns and responses to the stimuli based on the sensor data captured by the sensor devices 210.

Process 800 further includes detecting a deviation between actual stimuli response and expected stimuli response from the knowledge corpus (step 830). For example, as described above with respect to the knowledge corpus interface module 630 and the response deviation determination module 640, the health tracking server 225 access the knowledge corpus stored by the knowledge corpus server 220 to detect a deviation between the actual stimuli response (e.g., determined at step 820) and the expected stimuli response under similar environmental conditions (as determined at step 810). In this way, the health tracking server 225 detects a possible health issue with the unborn child.

Process 800 also includes determining a deviation instruction (step 840). For example, as described above with respect to the deviation instructions criteria repository 650, the health tracking server 225 determines deviation instructions based on the deviation instruction criteria stored by the deviation instructions criteria repository 650. As described herein, example deviation instructions/actions to take include modifying dosage settings and/or other operations of the medical device 230, interfacing with a computer-based scheduling system hosted by the medical device 230 to schedule an appointment with a medical professional, sending alerts to user devices associated with parents and/or medical professionals of the unborn child, etc. In embodiments, the health tracking server 225 determines deviation instructions only when a threshold number of deviations have been detected (e.g., at step 830) over a period of time. Additionally, or alternatively, the health tracking server 225 determined deviation instructions when the degree of the deviation exceed a threshold.

Process 800 further includes executing the deviation instructions (step 850). For example, as described above with respect to the deviation instruction execution module 660, the health tracking server 225 executes the deviation instructions (e.g., determined at step 840). In this way, the health tracking server 225 executes a corresponding action when a possible medical condition of an unborn child is detected (e.g., at step 830). As described herein, the deviation instruction includes a computer-executable instruction In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system/server 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
    monitoring, by a computing device, external stimuli and a set of environmental conditions exposed to an unborn child based on sensor data from a sensor device;
    identifying, by the computing device, the external stimuli exposed to the unborn child by utilizing the sensor data from crowd-sourced data, data from wearable devices, and/or external sensor data;
    monitoring, by the computing device, a response by the unborn child to the external stimuli based on another sensor data from another sensor device;
    detecting, by the computing device, a deviation between the response to the external stimuli and an expected response of the unborn child to the external stimuli, wherein the expected response to the external stimuli under the set of environmental conditions is determined based on information stored by a knowledge corpus, and the expected response indicates a response by a healthy child to the external stimuli under the set of environmental conditions; and
    executing, by the computing device, a deviation instruction based on the detected deviation to take a corresponding treatment-related action based on an indicated severity and type of medical condition,
    wherein the knowledge corpus comprises information describing movement and kick patterns with associated time stamps of other unborn children in response to the other unborn children being exposed to a predetermined stimuli and a predetermined set of environmental conditions, ultrasound scanned images of the other unborn children, an indication of whether the other unborn children are healthy or have the medical condition which corresponds with the movement and kick patterns of the other unborn children, an indicated severity and the type of the medical condition which corresponds with the movement and kick patterns of the other unborn children with the medical condition, and blood testing reports and a rate of change in blood flow and heart rate corresponding to the movement and kick patterns of the other unborn children.

2. The computer-implemented method of claim 1, further comprising determining the set of environmental conditions associated with the response to the external stimuli, wherein the detecting the deviation is further based on the response to the external stimuli under the set of environmental conditions deviating from the expected response to the external stimuli under the environment conditions and the deviation is indicative of hearing loss or vision loss in the unborn child.

3. The computer-implemented method of claim 1, further comprising detecting a number of deviations that meet a threshold number of deviations between the response to the external stimuli and an expected response of the unborn child to the external stimuli, wherein the executing the deviation instruction is further based on the detecting the number of deviations that meet the threshold number of deviations.

4. The computer-implemented method of claim 3, wherein the executing the deviation instruction is further based on the detecting the number of deviations that meet the threshold number of deviations within a threshold period of time.

5. The computer-implemented method of claim 1, further comprising determining the deviation instruction based on criteria, wherein the executing the deviation instruction is further based on the determined deviation instruction.

6. The computer-implemented method of claim 5, wherein the criteria includes:
 type of deviation;
 degree of the deviation;
 information regarding a health of a mother associated with the unborn child; and
 external data regarding the deviation.

7. The computer-implemented method of claim 1, wherein the deviation instruction includes:
 modifying a setting on a medical device;
 automatically sending an alert to a user device associated with a caretaker of the unborn child, the alert including the corresponding treatment-related action based on the indicated severity and the type of medical condition; and
 automatically scheduling an appointment with a medical professional and the caretaker of the unborn child.

8. The computer-implemented method of claim 1, wherein the knowledge corpus includes a plurality of historical data records identifying different responses from the other unborn children to different sets of external stimuli under different environmental conditions than the set of environmental conditions.

9. The computer-implemented method of claim 8, wherein the plurality of data records included in the knowledge corpus identifies corresponding health conditions associated with the different responses to different sets of external stimuli under the different environmental conditions.

10. The computer-implemented method of claim 1, wherein a service provider at least one of creates, maintains, deploys and supports the computing device.

11. The computer-implemented method of claim 1, wherein the monitoring the external stimuli, the monitoring the response to the external stimuli, the detecting the deviation, and the executing the deviation instruction are provided by a service provider on a subscription, advertising, and/or fee basis.

12. The computer-implemented method of claim 1, wherein the computing device includes software provided as a service in a cloud environment.

13. The computer-implemented method of claim 1, further comprising deploying a system, wherein the deploying the system comprises providing a computer infrastructure operable to perform the monitoring the external stimuli, the monitoring the response to the external stimuli, the detecting the deviation, and the executing the deviation instruction.

14. A computer program product comprising a computer readable storage medium having program instructions embodied therewith, the program instructions executable by a computing device to cause the computing device to:
 receive and monitor sensor data from a sensor device corresponding to movement patterns of an unborn child;
 identify external stimuli and a set of environmental conditions associated with the movement patterns based on another sensor data from another sensor device from crowd-sourced data, data from wearable devices, and/or external sensor data;
 generate a plurality of records, each having a dataset identifying the external stimuli, corresponding movement patterns associated with the external stimuli, the set of environmental conditions, and health condition information;
 provide the plurality of records for storage in a knowledge corpus;
 identify a health condition in a different unborn child based on actual responses to the external stimuli and expected responses to the external stimuli under the set of environmental conditions stored by the knowledge corpus, wherein the expected response indicates a response by a healthy child to the external stimuli under the set of environmental conditions; and
 execute a corresponding treatment-related action based on the identified health condition,
 wherein the knowledge corpus comprises information describing movement and kick patterns with associated time stamps of other unborn children in response to the other unborn children being exposed to a predetermined stimuli and a predetermined set of environmental conditions, ultrasound scanned images of the other unborn children, an indication of whether the other unborn children are healthy or have the medical condition which corresponds with the movement and kick patterns of the other unborn children, an indicated severity and the type of the medical condition which corresponds with the movement and kick patterns of the other unborn children with the medical condition, and blood testing reports and a rate of change in blood flow and heart rate corresponding to the movement and kick patterns of the other unborn children.

15. The computer program product of claim 14, wherein the action includes:
 modifying a setting on a medical device;
 automatically sending an alert to a user device associated with a caretaker of the unborn child, the alert including the corresponding treatment-related action based on the indicated severity and the type of medical condition; and
 automatically scheduling an appointment with a medical professional and the caretaker of the unborn child.

16. The computer program product of claim 14, wherein the program instructions further cause the computing device to determine the set of environmental conditions associated with the external stimuli, wherein the plurality of records further identify the set of environmental conditions associated with the external stimuli.

17. The computer program product of claim 14, wherein:
 the identifying the health condition comprises detecting a deviation between the actual responses to the external stimuli and expected responses to the external stimuli; and
 the health condition is hearing loss or vision loss in the unborn child and the deviation is indicative of the hearing loss or vision loss.

18. A The computer program product of claim 17, wherein the identifying the health condition comprises detecting greater than a threshold number of deviations between the actual responses to the external stimuli and expected responses to the external stimuli.

19. A system comprising:
a processor, a computer readable memory and a computer readable storage medium associated with a computing device;
program instructions to identify, based on sensor data gathered by one or more sensor devices from crowd-sourced data, data from wearable devices, and/or external sensor data, an external stimuli and actual responses to the external stimuli by an unborn child under a set of environmental conditions;
program instructions to identify a health condition in the unborn child based on a deviation between the actual responses to external stimuli and expected responses to the external stimuli under the set of environmental conditions, wherein the expected responses to the external stimuli under the set of environmental conditions are stored in a knowledge corpus, and the expected response indicates a response by a healthy child to the external stimuli under the set of environmental conditions;
program instructions to execute a computer-executable instruction to take a corresponding treatment-related action based on the identifying the health condition including a severity and a type of the health condition,
wherein the program instructions are stored on the computer readable storage medium for execution by the processor via the computer readable memory, and
the knowledge corpus comprises information describing movement and kick patterns with associated time stamps of other unborn children, ultrasound scanned images of the other unborn children, and blood testing reports and a rate of change in blood flow and heart rate corresponding to the movement and kick patterns of the other unborn children.

20. The system of claim 19, wherein the computer-executable instruction includes:
modifying a setting on a medical device;
automatically sending an alert to a user device associated with a caretaker of the unborn child, the alert including the corresponding treatment-related action based on the indicated severity and type of medical condition; and
automatically scheduling an appointment with a medical professional and the caretaker of the unborn child.

* * * * *